US006951557B2

(12) United States Patent
Ellis et al.

(10) Patent No.: US 6,951,557 B2
(45) Date of Patent: *Oct. 4, 2005

(54) PERCUTANEOUS MYOCARDIAL REVASCULARIZATION DEVICE AND METHOD

(75) Inventors: Louis Ellis, St. Anthony, MN (US); Daniel M. Lafontaine, Plymouth, MN (US); Roger N. Hastings, Maple Grove, MN (US); Lauri DeVore, Seattle, WA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 51 days.

This patent is subject to a terminal disclaimer.

(21) Appl. No.: 10/231,033

(22) Filed: Aug. 30, 2002

(65) Prior Publication Data

US 2002/0193782 A1 Dec. 19, 2002

Related U.S. Application Data

(60) Continuation of application No. 09/536,068, filed on Mar. 24, 2000, now Pat. No. 6,491,689, which is a division of application No. 09/035,625, filed on Mar. 5, 1998, now Pat. No. 6,056,743.
(60) Provisional application No. 60/064,169, filed on Nov. 4, 1997.

(51) Int. Cl.[7] .............................................. A61B 18/18
(52) U.S. Cl. ............................. 606/15; 606/7; 606/13; 606/14; 606/78; 607/88; 607/89; 604/21
(58) Field of Search .............................. 606/7, 13–16, 606/78, 167; 607/88, 89; 604/19–22

(56) References Cited

U.S. PATENT DOCUMENTS

| 4,790,311 A | 12/1988 | Ruiz .................. 128/303.1 |
| 4,896,671 A | 1/1990 | Cunningham et al. ...... 128/642 |
| 5,047,026 A | 9/1991 | Rydell ..................... 606/48 |

(Continued)

FOREIGN PATENT DOCUMENTS

| DE | 296 09 350 U1 | 10/1996 |
| DE | 195 37 084 A1 | 4/1997 |
| WO | WO 96/35469 | 11/1996 |
| WO | WO 96/39963 | 12/1996 |
| WO | WO 97/18768 | 5/1997 |
| WO | WO 97/29803 | 8/1997 |
| WO | WO 9732551 | 9/1997 |
| WO | WO 97/44071 | 11/1997 |
| WO | WO 00/18307 | 4/2000 |

OTHER PUBLICATIONS

Mirhoseini et al. Abstract entitled "Transventricular Revascularization by Laser", *Lasers in Surgery and Medicine*, 2(2), 1982, 1 pg.

(Continued)

*Primary Examiner*—A. Farah
(74) *Attorney, Agent, or Firm*—Kenyon & Kenyon

(57) ABSTRACT

Devices and methods for creating a series of percutaneous myocardial revascularization (PMR) channels in the heart. One method includes forming a pattern of channels in the myocardium leading from healthy tissue to hibernating tissue. Suitable channel patterns include lines and arrays. One method includes anchoring a radiopaque marker to a position in the ventricle wall, then using fluoroscopy repeatedly to guide positioning of a cutting tip in the formation of multiple channels. Another method uses radiopaque material injected into each channel formed, as a marker. Yet another method utilizes an anchorable, rotatable cutting probe for channel formation about an anchor member, where the cutting probe can vary in radial distance from the anchor. Still another method utilizes a multiple wire radio frequency burning probe, for formation of multiple channels simultaneously. Still another method utilizes liquid nitrogen to cause localized tissue death.

9 Claims, 8 Drawing Sheets

U.S. PATENT DOCUMENTS

| | | | | |
|---|---|---|---|---|
| 5,093,877 | A | 3/1992 | Aita | 385/34 |
| 5,106,386 | A | 4/1992 | Isner et al. | 606/15 |
| 5,358,485 | A | 10/1994 | Vance et al. | 604/22 |
| 5,364,393 | A | 11/1994 | Auth et al. | 606/34 |
| 5,370,675 | A | 12/1994 | Edwards et al. | 607/101 |
| 5,380,316 | A | 1/1995 | Aita et al. | 606/7 |
| 5,389,096 | A | 2/1995 | Aita et al. | 606/15 |
| 5,403,311 | A | 4/1995 | Abele et al. | 606/49 |
| 5,423,804 | A | 6/1995 | Kulick | 606/14 |
| 5,437,660 | A | 8/1995 | Johnson et al. | 606/15 |
| 5,498,258 | A | 3/1996 | Hakky et al. | 606/15 |
| 5,522,815 | A | 6/1996 | Durgin, Jr. et al. | 606/50 |
| 5,591,159 | A | 1/1997 | Taheri | 606/15 |
| 5,593,405 | A | 1/1997 | Osypka | 606/15 |
| 5,607,405 | A | 3/1997 | Decker et al. | 604/264 |
| 5,620,414 | A | 4/1997 | Campbell, Jr. | 604/22 |
| 5,672,174 | A | 9/1997 | Gough et al. | 606/41 |
| 5,681,308 | A | 10/1997 | Edwards et al. | 606/41 |
| 5,683,366 | A | 11/1997 | Eggers et al. | 606/41 |
| 5,697,882 | A | 12/1997 | Eggers et al. | 604/114 |
| 5,700,259 | A | 12/1997 | Negus et al. | 606/14 |
| 5,703,985 | A | 12/1997 | Owyang | 385/117 |
| 5,713,894 | A | 2/1998 | Murphy-Chutorian et al. | 606/15 |
| 5,725,521 | A | 3/1998 | Mueller | 606/7 |
| 5,725,523 | A | 3/1998 | Mueller | 606/15 |
| 5,738,680 | A | 4/1998 | Mueller et al. | 606/15 |
| 5,755,714 | A * | 5/1998 | Murphy-Chutorian | 606/15 |
| 5,769,843 | A | 6/1998 | Abela et al. | 606/10 |
| 5,782,823 | A | 7/1998 | Mueller | 606/7 |
| 5,782,824 | A | 7/1998 | Abela et al. | 606/15 |
| 5,840,075 | A | 11/1998 | Mueller et al. | 606/7 |
| 5,855,577 | A * | 1/1999 | Murphy-Chutorian et al. | 606/7 |
| 5,871,495 | A | 2/1999 | Mueller | 606/185 |
| 5,873,865 | A * | 2/1999 | Horzewski et al. | 604/523 |
| 5,878,751 | A | 3/1999 | Hussein et al. | 128/898 |
| 5,910,150 | A | 6/1999 | Saadat | 606/159 |
| 5,957,916 | A * | 9/1999 | Jeevanandam et al. | 606/15 |
| 6,036,685 | A | 3/2000 | Mueller | 606/15 |
| 6,042,581 | A | 3/2000 | Ryan et al. | 606/45 |
| 6,045,565 | A | 4/2000 | Ellis et al. | 606/167 |
| 6,053,911 | A | 4/2000 | Ryan et al. | 606/33 |
| 6,056,743 | A * | 5/2000 | Ellis et al. | 606/15 |
| 6,063,082 | A | 5/2000 | DeVore et al. | 606/45 |
| 6,066,131 | A | 5/2000 | Mueller et al. | 606/15 |
| 6,491,689 | B1 * | 12/2002 | Ellis et al. | 606/15 |

OTHER PUBLICATIONS

Gal et al., Abstract entitled "Analysis of Photoproducts Free Radicals and Particulate Debris Generated . . . ", *Lasers in Surgery and Medicine,* 11(2) 1991, 1 pg.

Isner, J., Abstract entitled "Right Ventricular Myocardial Infarction", *JMAA,* v259, n5, Feb. 5, 1988, 12 pgs.

Pickering et al., Abstract entitled "Proliferactive Activity in Peripheral and Coronary Atherosclerotic Plaque . . . ", *J. Clin. Invest.,* ISSN 0021–9738, Apr. 1993, 1 pg.

Vineberg et al., "Creation of Intramyocardial Pathways to Channel Oxygenated Blood Between Ventricular Arteriolar Zones", *Canad. Med. Ass. J.,* vol. 96, Feb. 4, 1967, 3 pgs.

Vineberg et al., "Results of 14 Years'Experience in the Surgical Treatment of Human Coronary Artery Insufficiency", *Canad. Med. Ass. J.,* vol. 92, Feb. 13, 1965, 8 pgs.

Vineberg et al., "The Ivalon Sponge Procedure for Myocardial Revascularization", *Surgery,* vol. 47, No. 2, Feb. 1960, pp. 268–289.

Vineberg et al., "Treatment of Acute Myocardial Infarction by Endocardial Resection", *Surgery,* vol. 57, No. 6, Jun. 1965, pp. 832–835.

Walter et al., "Treatment of Acute Myocardial Infarction by Transmural Blood Supply from the Ventricular Cavity", *European Surgical Research,* 3:130–138, 1971.

Khazei et al., "Myocardial Canalization", *The Annals of Thoracic Surgery,* vol. 6, No. 2, Aug. 1968, pp. 163–171.

Hershey et al., "Transmyocardial Puncture Revascularization", *Geriatrics,* Mar. 1969, pp. 101–108.

Press Release dated Oct. 21, 1996, "Doctors Demonstrate Proof of Blood Flow Through Open TMR Channels Created with PLC Systems . . . ", t pg.

Press/News Release dated Oct. 10, 1996, Texas Fieart Institute Presents Study Comparing the Use of CO2 . . . :, 1 pg.

Goldman et al., "Nonoperative Portacaval Shunt in Swing", *Investigative Radiology,* vol. 25, No. 5, May 1990, 5 pgs.

* cited by examiner

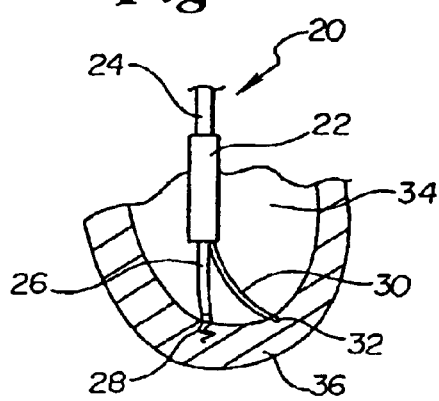
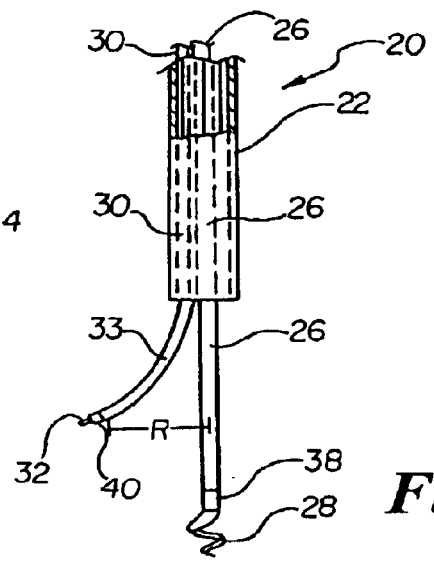
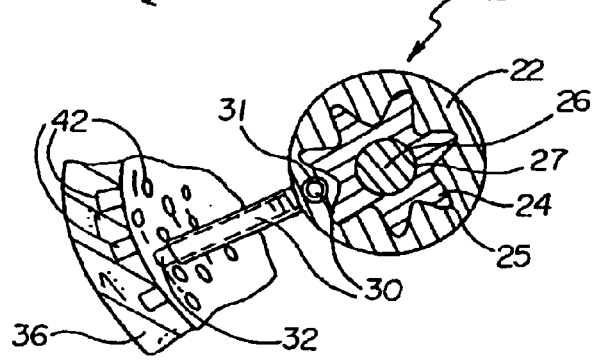
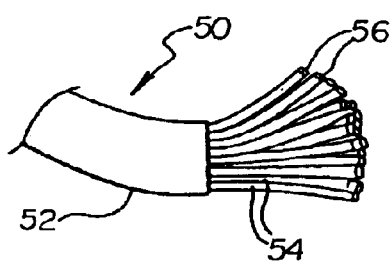
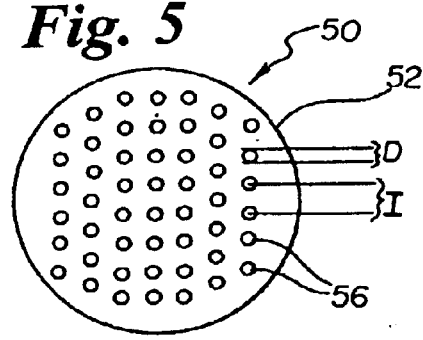

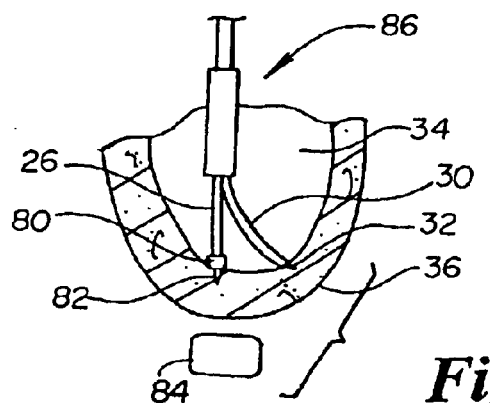
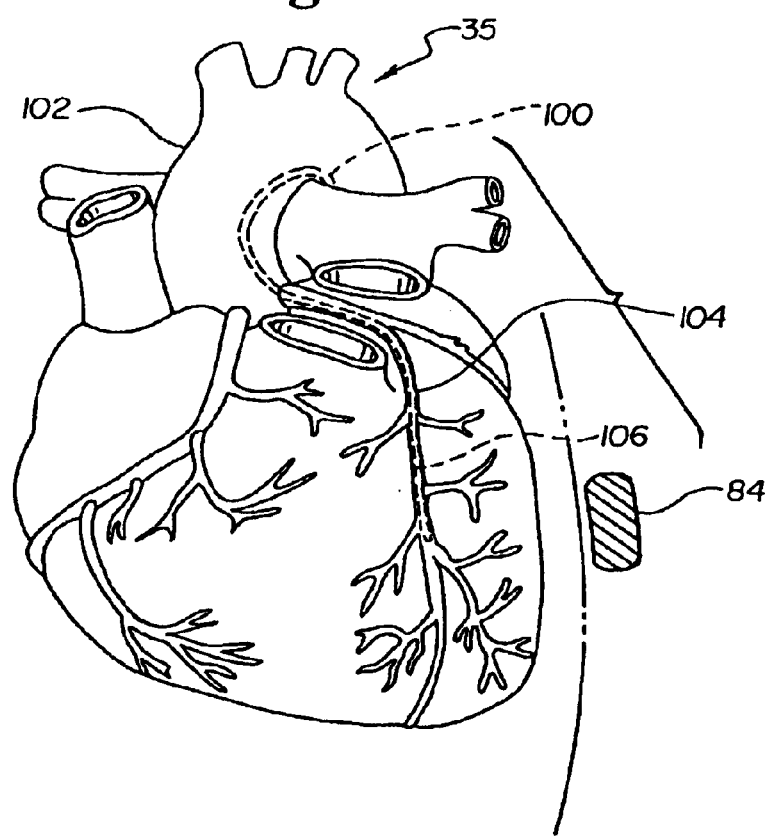

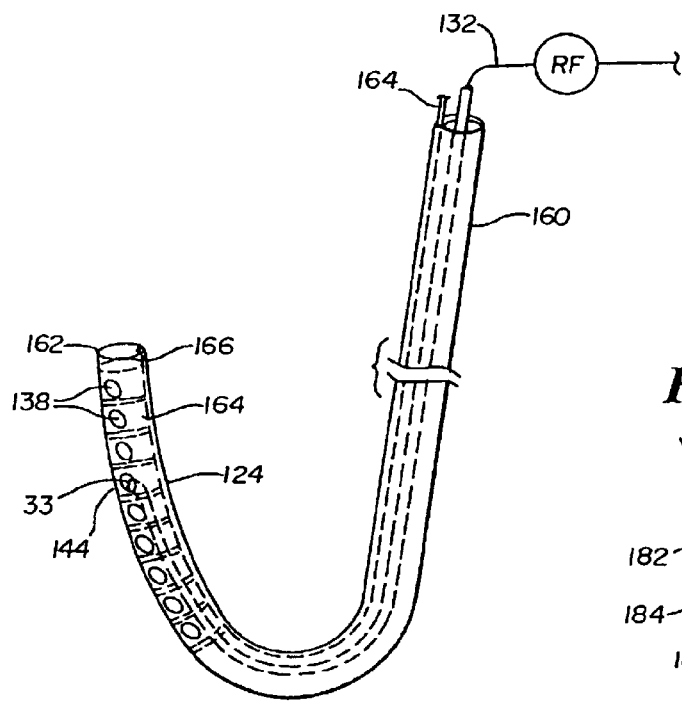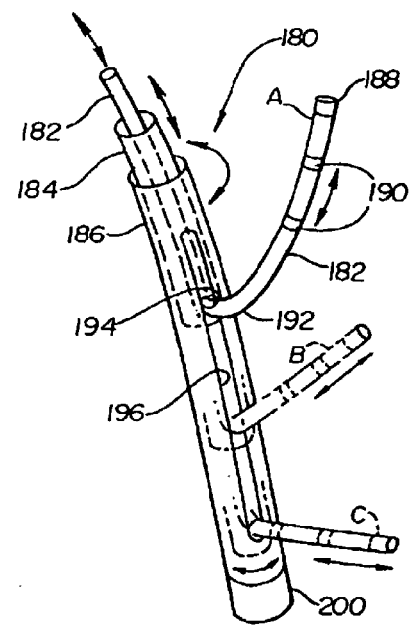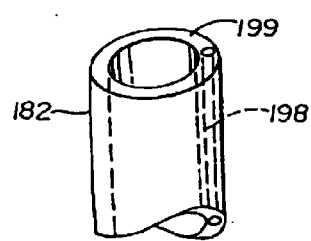

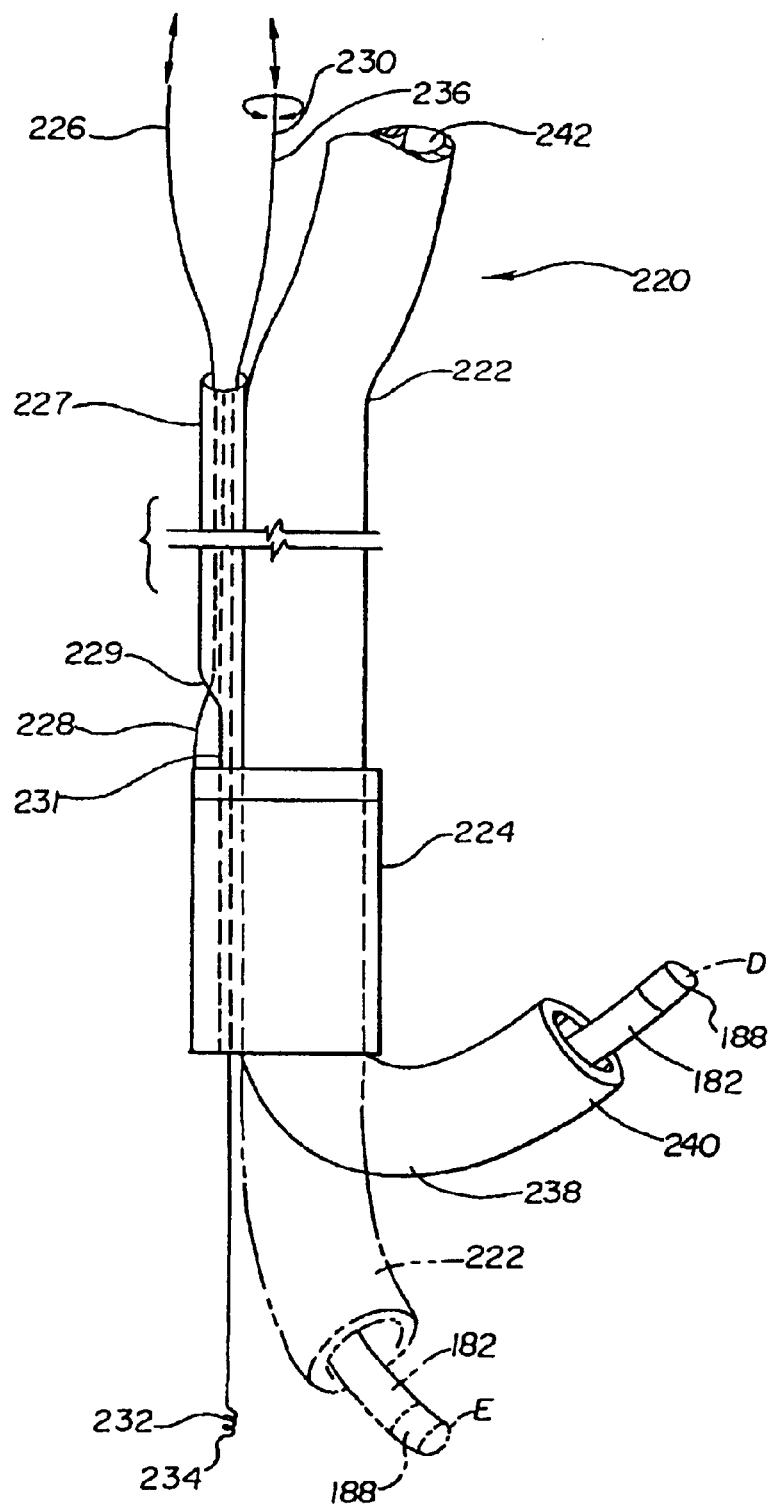

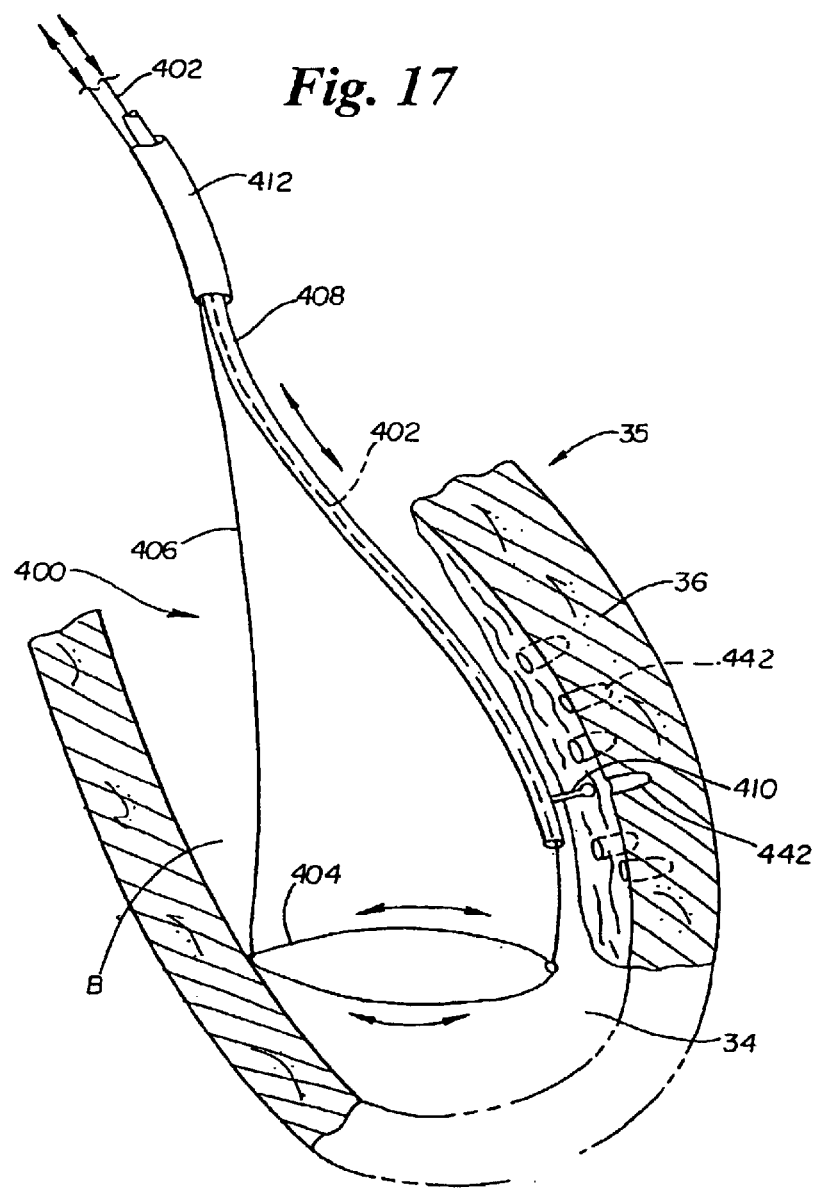
*Fig. 17*
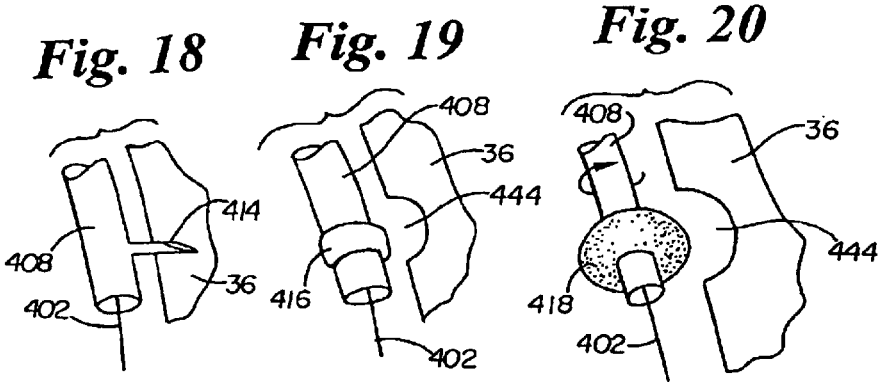
*Fig. 18*  *Fig. 19*  *Fig. 20*

PERCUTANEOUS MYOCARDIAL REVASCULARIZATION DEVICE AND METHOD

CROSS REFERENCE TO RELATED APPLICATION

The present application is a Continuation of application Ser. No. 09/536,068 which was filed on Mar. 24, 2000, now U.S. Pat. No. 6,491,689, which is a division of application Ser. No. 09/035,625 filed Mar. 5, 1998, now U.S. Pat. No. 6,056,743, and claims the benefit of U.S. Provisional Patent Application No. 60/064,169, filed Nov. 4, 1997.

FIELD OF THE INVENTION

The present application is related to devices and methods for promoting blood circulation to the heart muscle. Specifically, the present invention is related to percutaneous myocardial revascularization (PMR) devices and methods for forming multiple channels in the myocardium.

BACKGROUND OF THE INVENTION

A number of techniques are available for treating cardiovascular disease such as cardiovascular by-pass surgery, coronary angioplasty, laser angioplasty and atherectomy. These techniques are generally applied to by-pass or open lesions in coronary vessels to restore and increase blood flow to the heart muscle. In some patients, the number of lesions are so great, or the location so remote in the patient vasculature that restoring blood flow to the heart muscle is difficult. Percutaneous myocardial revascularization (PMR) has been developed as an alternative to these techniques which are directed at by-passing or removing lesions.

Heart muscle may be classified as healthy, hibernating and "dead". Dead tissue is not dead but is scarred, not contracting, and no longer capable of contracting even if it were supplied adequately with blood. Hibernating tissue is not contracting muscle tissue but is capable of contracting, should it be adequately re-supplied with blood. PMR is performed by boring channels directly into the myocardium of the heart.

PMR was inspired in part by observations that reptilian hearts muscle is supplied primarily by blood perfusing directly from within heart chambers to the heart muscle. This contrasts with the human heart, which is supplied by coronary vessels receiving blood from the aorta. Positive results have been demonstrated in some human patients receiving PMR treatments. These results are believed to be caused in part by blood flowing from within a heart chamber through patent channels formed by PMR to the myocardial tissue. Suitable PMR channels have been burned by laser, cut by mechanical means, and burned by radio frequency current devices. Increased blood flow to the myocardium is also believed to be caused in part by the healing response to wound formation. Specifically, the formation of new blood vessels is believed to occur in response to the newly created wound.

What remains to be provided are improved methods and devices for increasing blood perfusion to the myocardial tissue. What remains to be provided are methods and devices for increasing blood flow to myocardial tissue through controlled formation of channel patterns in the myocardium.

SUMMARY OF THE INVENTION

The present invention includes devices and methods for creation of multiple holes in the myocardium of a human heart for percutaneous myocardial revascularization. A pattern of holes is optimally created extending from healthy tissue to hibernating tissue, thereby increasing the supply of blood to hibernating heart muscle tissue. Creating a controlled pattern of channels rather than simply a plurality of channels of unknown location can be accomplished using various methods and devices. Holes can be considered the space left after a volumetric removal of material from the heart wall. Channels have a depth greater than their width and craters have a width greater than their depth.

One method includes marking a first location in the heart muscle wall with a radiopaque marker, then positioning a radiopaque cutting tip relative to the radiopaque marker using fluoroscopy and cutting channels in the myocardium where appropriate. Suitable markers can be secured to the endocardium mechanically with barbs or pigtails or injected into the myocardium. Suitable channel patterns include lines, arrays, and circular clusters of channels.

Another method includes injecting radiopaque material into the newly formed channels, thereby marking the positions of the channels already formed. The radiopaque material should be held in place with polymeric adhesives for the duration of the treatment. The channels formed can be viewed under fluoroscopy using this method. The marker can remain throughout the procedure or only long enough to record the position for mapping.

Yet another method can be accomplished by providing a myocardial channel forming device having an anchoring member, a treatment member with a cutting tip, means for rotating the cutting member about the anchoring member, and means for controlling the radial displacement of the cutting tip from the anchoring member. The anchoring member can be implanted in a heart chamber wall using a pigtail, and the radial and rotational displacement of the cutting tip controlled to sequentially form a circular cluster of channels about the anchoring member. The circular cluster preferably includes both healthy and hibernating tissue areas, which can be mapped using conventional techniques. A variant of this technique utilizes a device having a spline and corresponding star shaft, which restricts the number of possible rotational angles and provide predictable arc rotations around the spline for the treatment member about the anchoring shaft.

Still another method utilizes a bundle of fibers within a sheath as the cutting device. Preferred fibers are formed of Nitinol wire and carry radio frequency current to effect burning channels in the myocardium. Optical fibers carrying laser light for burning are used in another embodiment. The splay of fibers out of the distal end of the sheath can be controlled by controlling the bias of the fibers. The bias of the fibers can be controlled by utilizing shape memory materials, such as Nitinol wire. The splay of fibers can also be controlled by controlling the length of fiber exposed at the distal end, by controlling the retraction of the sheath over the fibers.

A variant device utilizes a magnetically responsive anchoring member, which can be pulled against the heart wall by an external magnetic force. The heart wall can have movement lessened during this procedure and other procedures generally, by inserting a catheter having a magnetically responsive distal region into a coronary artery. Force can be brought to bear upon the heart wall region having the catheter disposed within by applying a magnetic force on the catheter. The applied force can exert a pulling force on the catheter, reducing movement of the beating heart wall in that region.

Another device includes an outer positioning tube having several side channels in the distal region and means for securing the distal region against movement within the heart chamber. One securing means includes a suction orifice near the distal end supplied with vacuum by a vacuum lumen extending the length of the outer tube. Another securing means includes a magnetically responsive portion of the outer tube. The suction orifice can be secured to the heart chamber wall by applying vacuum and the magnetically responsive portion can be forced into the chamber wall by applying an external magnet field. The inner tube can contain an intermediate guide tube and the guide tube can contain an inner PMR cutting wire with a arcuate biased distal region. As the arcuate distal region is moved through the outer tube distal region and over the side channels, the PMR wire distal region can extend through a side channel and to the heart chamber wall. The PMR wire can be moved past undesired side holes by rotating the wire such that the arcuate wire region is oriented away from the side holes.

Another device includes a tube-in-a-tube configuration, having an outer tube disposed about an intermediate tube disposed about an inner PMR cutting probe. The inner PMR probe can be performed to have a distal region arcuate or angled bias, bent away from the longitudinal axis of the probe. The PMR probe distal region can extend through a side channel in the distal region of the intermediate tube and is slidable within the intermediate tube, thereby exposing a varying length of distal PMR probe outside of the intermediate tube. The intermediate tube is slidably disposed within the outer tube which has an elongate slot to allow passage of the PMR probe therethrough. Thus, the radial extent or length of extending PMR probe can be varied by sliding the PMR probe within the intermediate and outer tubes, the longitudinal position of the PMR probe can be varied by sliding the intermediate tube within the outer tube, and the rotational position can be varied by rotating the outer tube from the proximal end. Varying the amount of a performed, bent PMR probe extending from the intermediate tube can also change the longitudinal position of the PMR probe distal end.

Another device includes an elongate rod having a distal region secured to an outer collar, such that the outer collar can be pushed and pulled. The outer collar is slidably disposed over an intermediate tube. An inner PMR cutting probe is slidably disposed within the intermediate tube. The inner PMR probe and intermediate tube together have a distal region arcuate or bent bias or perform, such that distally advancing the outer collar over the intermediate tube straightens out the intermediate tube and proximally retracting the outer collar allows the arcuate bias or bend to be exhibited in the distal region shape of PMR probe and intermediate tube. The perform can exist in the PMR probe, intermediate tube, or both. The device includes means for anchoring the device to the ventricle wall. Circles or arcs of myocardial channels can be formed by rotating the outer tube, extending the inner PMR probe, and varying the amount of arc to form distal of the outer collar.

Yet another device includes an anchoring member and a positionable cryanoblative treatment tube. The treatment tube can be formed of metal and be either closed or open ended. In use, the device is anchored within a heart chamber and a cryogenic substance such a liquid nitrogen delivered through the tube and to the tube distal end. The liquid nitrogen can cause localized tissue death, bringing about the desired healing response. Still another device includes a plurality of splayed, cryanoblative tubes within a sheath. The tubes can be supplied with liquid nitrogen, which can be delivered through the tube lumens to the tube distal ends so as to cause localized myocardial tissue death at multiple sites substantially simultaneously.

In yet another embodiment, a catheter assembly is provided including a guide wire having a proximal end and a distal end. An expandable member, which may be a wire loop, is disposed at the distal end of the guide wire. The expandable member is moveable between a first position and a second position. In the first position, the member is collapsed to move through a lumen of a guide catheter. In a second position, the expandable member has a transverse diameter, with respect to the length of the guide wire, greater than the transverse diameter of the guide catheter lumen. An elongate catheter having a proximal end and a distal end is disposed on the guide wire. A therapeutic device is connected to the distal end of the catheter. The therapeutic device can be a needle, hypotube, electrode or abrasive burr to form holes or craters in the myocardium of the patient's heart.

BRIEF DESCRIPTION OF THE DRAWINGS

FIG. 1 is a fragmentary, side, cutaway view of a left ventricle having an anchorable, positionable PMR device within;

FIG. 2 is a fragmentary, side view of the PMR device of FIG. 1, showing anchor and treatment members is phantom within a catheter shaft;

FIG. 3 is a top view of the PMR catheter and ventricle of FIG. 1, showing a transverse cross-sectional view of the PMR catheter and a fragmentary cross-section and projection of the ventricle wall;

FIG. 4 is a fragmentary, perspective view of a multiple-tip PMR treatment device according to the present invention;

FIG. 5 is an end view of the multiple-tip PMR treatment device of FIG. 4;

FIG. 6 is a fragmentary, side, cutaway view of a left ventricle having a magnetically anchorable, positionable PMR device within;

FIG. 8 is a perspective view of a heart having a magnetic, heart wall stabilizing catheter disposed within the left coronary artery, shown in phantom;

FIG. 10 is a fragmentary, perspective view of a device related to the device of FIG. 9, illustrated without distal anchoring means, better illustrating a shape member within the device;

FIG. 11 is a perspective view of a tube-in-a-tube positioning device for positioning a PMR cutting probe, having an outer tube containing an inner tube containing a PMR cutting probe;

FIG. 12 is a fragmentary, perspective view of a section through the PMR probe of FIG. 11, better illustrating the shape member;

FIG. 13 is a perspective view of an extendable collar device for positioning a PMR probe, having a slidable collar over an intermediate tube over a PMR cutting probe;

FIG. 17 is a view of the device of FIG. 16 in use;

FIG. 18 is an alternate embodiment of the device of FIG. 16;

FIG. 19 is an alternate embodiment of the device of FIG. 16; and

FIG. 20 is an alternate embodiment of the device of FIG. 16.

DETAILED DESCRIPTION OF THE PREFERRED EMBODIMENTS

Figure 7:
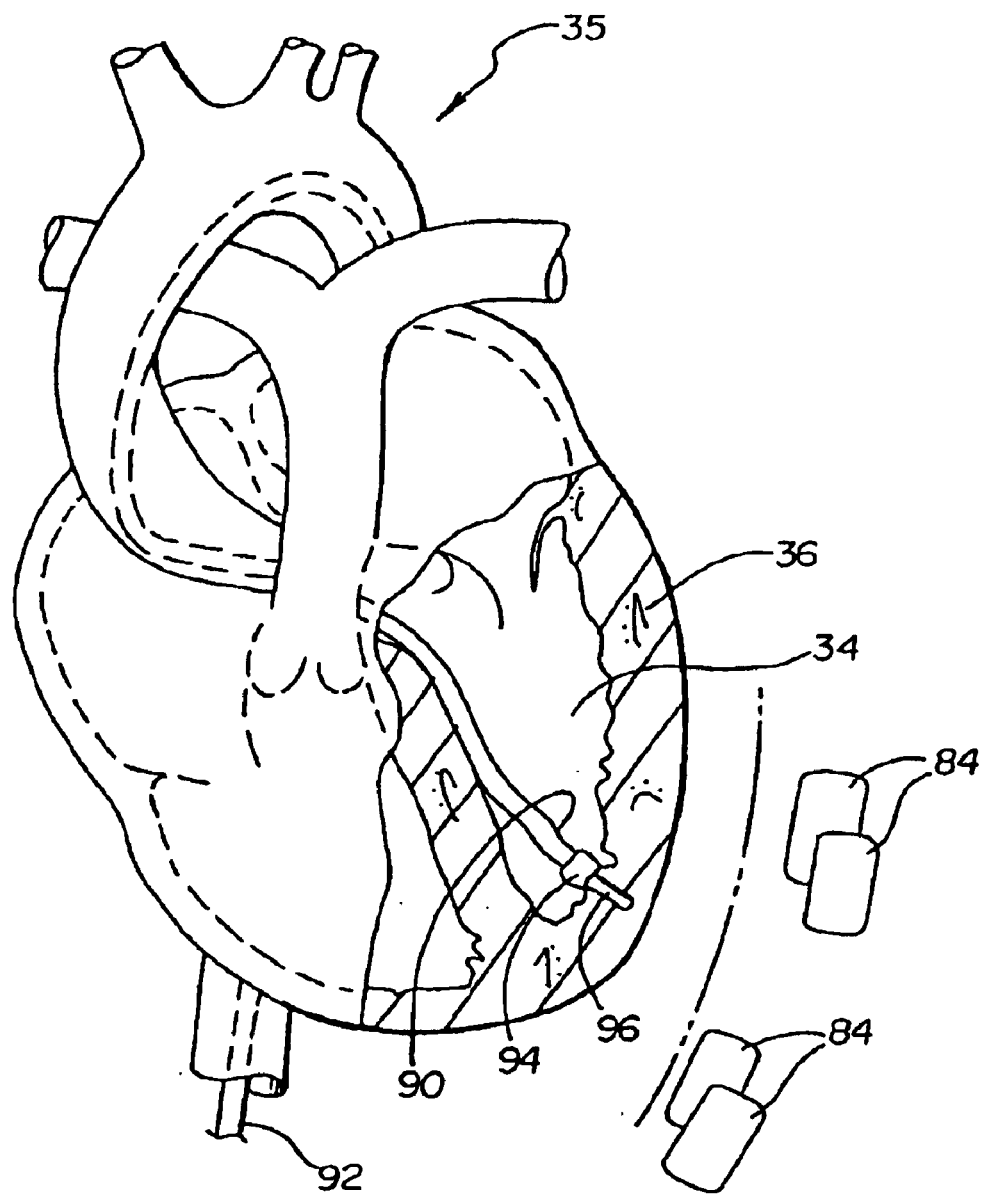
FIG. 7 is cutaway, perspective view of a heart having a magnetically positionable PMR cutting tip within the left ventricle wall.

FIG. 1 illustrates an anchorable percutaneous myocardial revascularization (PMR) treatment catheter 20 disposed within a left ventricle 34. PMR catheter 20 includes an inner star shaft 24 disposed within an outer catheter shaft 22, an anchoring shaft 26 disposed within star shaft 24, and a treatment shaft or probe 30 disposed within catheter shaft 22. Catheter shaft 22 has been cut away proximally in FIG. 1, illustrating inner star shaft 24 within. Anchoring shaft 26 has an anchor 28 disposed at the distal end. In a preferred embodiment, anchor 28 has a pigtail or corkscrew configuration, capable of reversibly securing itself to the ventricular wall through rotation of anchoring shaft 26. One embodiment anchor includes a distal barb, capable of securing itself to the ventricular wall through translation of anchoring shaft 26, not requiring shaft rotation for anchoring. In another embodiment, anchoring shaft 26 includes a vacuum lumen therethrough terminating in a distal orifice or suction tip (not shown). Treatment shaft 30 has a distal cutting tip 32, shown embedded within a section of a left ventricular wall 36. The term "cutting" as used herein includes penetrating and channel forming by other means.

Referring now to FIG. 2, PMR catheter 20 is illustrated in more detail. Anchor shaft 26, extending through outer catheter shaft 22, includes a distal radiopaque marker 38. Treatment shaft 30, extending through catheter tube 22, preferably includes an arcuate, distal region 33 and a distal radiopaque marker 40. Radiopaque markers 38 and 40 can aid in determining the positions of the anchoring and treatment shafts under fluoroscopy. Suitable radiopaque materials are well known to those skilled in the art, including barium, bismuth, tungsten and platinum. Referring now to FIG. 3, PMR catheter 20 is illustrated in a top, cross-sectional view taken through the catheter. In a preferred embodiment, anchoring shaft 26 is contained within an anchor shaft lumen 27. Anchor shaft lumen 27 is preferably slidably disposed within an inner shaft such as star shaft 24. Inner shaft 24 preferably has a star shape and is disposed within a star lumen 25 having internal splines corresponding to the vertices of star shaft 24. Treatment shaft 30 is preferably slidably disposed within a treatment shaft lumen 31 within the wall of PMR outer shaft 22. As illustrated, treatment shaft 30 cutting end 32 has formed several channels 42 in the myocardium of ventricular wall 36.

The use of PMR device 20 may now be discussed, with reference to FIGS. 1, 2 and 3. Several degrees of freedom of movement of cutting tip 32 are possible with the present invention. Treatment shaft distal region 33 is preferably biased to assume a more radially extended position when unconstrained by lumen 31. Cutting tip 32 may be seen to have a radial distance "R" from anchoring shaft 26, as indicated in FIG. 2. Holding the axial displacement of anchoring shaft 26 and treatment shaft 30 fixed while distally, axially sliding catheter outer shaft 22 over both shafts 26 and 30 causes more of treatment shaft distal region 33 to be drawn into outer shaft 22, thereby decreasing the radial distance R of cutting tip 32 from anchoring shaft 26. Thus, by proximally fixing the longitudinal positions of anchoring shaft 26 and treatment shaft 30, and sliding outer shaft 26 over a range of motion, a series of channels along a line extending radially outward from anchoring shaft 26 can be created. It will be recognized that, to the extent the inner ventricular wall does not match the arcuate shape of treatment shaft distal region 33, it may be necessary to adjust the longitudinal displacement of treatment shaft 30 within outer shaft 22 as well, to enable cutting tip 32 to reach the endocardium.

In addition to cutting a series of channels radially outward from anchoring shaft 26, cutting tip 32 can also describe an arc about treatment shaft lumen 31, best visualized with reference to FIG. 3. By rotating treatment shaft 30 within lumen 31, cutting tip 32 can sweep through an arc, cutting a regular series of channels into the myocardium. By varying radial distance R and the rotation of treatment shaft 30, a regular series of arcs of channels can be formed, with the arcs having increasing radial distance from outer shaft 22.

Outer shaft 22 can also be rotated relative to anchoring shaft 26, thereby enabling the cutting of a regular series of channels in a circle about anchoring shaft 26. In a preferred embodiment, an intermediate star shaft such as shaft 24 is disposed between anchoring shaft 26 and outer shaft 22. Star shaft 24 can serve to restrict the rotational positions possible for outer shaft 22 relative to inner, anchoring shaft 26. Outer shaft 22 having internal splines, is not freely rotatable about the vertices of start shaft 24. In order for outer shaft 22 and carried treatment shaft 30, to be rotated about anchor shaft 26, star shaft 24 can be star shaped only is a limited distal region, and outer shaft 22 only splined in a limited distal region. In a preferred embodiment, star shaft 24 and outer shaft 22, at a location proximal of the cross section of FIG. 3, have smooth outer and inner surfaces, respectively. The smooth surfaces allow star shaft 24 to be rotated within outer shaft 22 when star shaft 24 has been retracted proximally into the smooth region. After rotation, star shaft 24 can be advanced distally, sliding within a spline of outer shaft 22. The rotation of outer shaft 22 can thus be restricted when desired and enabled when desired. When enabled, rotation of shaft 22 can thus be restricted to a discrete set of rotational angles. Another embodiment of the invention dispenses with intermediate, start shaft 24, allowing outer shaft 22 to rotate directly about inner, anchoring shaft 26. In this embodiment, the rotation of outer shaft 22 about anchoring shaft 26 is not restricted to a set of discrete rotational angles.

Cutting tip 32 can form a substantially regular pattern of channels. Cutting tip 32 preferably is formed of a wire such as Nitinol or elgiloy or stainless steel, and is capable of delivering the radio frequency current used for cutting channels in the myocardium. A suitable device for radio frequency cutting is described in co-pending U.S. patent application Ser. No. 08/810,830, filed Mar. 6, 1997, entitled RADIOFREQUENCY TRANSMYOCARDIAL REVASCULARIZATION APPARATUS AND METHOD. By restricting the movement of cutting tip 32 to movements relative to anchor tip 28, a more regular pattern of channels can be formed, even with limited fluoroscopic feedback, relative to the pattern formed by a cutting tip operating independent of the anchoring tip.

Referring now to FIG. 4, a multi-fiber treatment probe 50 is illustrated. Treatment probe 50 includes a plurality of wires or optical fibers 54, having distal cutting tips 56, and enclosed within a sheath 52. FIG. 5 illustrates and end view of multi-fiber probe 50, showing distal cutting tips 56 in the pattern they would have approaching the myocardium. Probe 50 allows a pattern of channels to be formed in the myocardium at the same time, not requiring repeated re-positioning of a single cutting tip such as cutting tip 32 of FIG. 2. Wires 54 are preferably formed of Nitinol wire. Use of a bundle of fibers including metal wires or optical fibers allows use of RF or laser cutting means, respectively. RF and laser cutting allows use of fibers relatively close together, as illustrated in FIG. 5. Mechanical cutting tips, such as those using rotating cutting blades, can require more space between cutting tips, not allowing the dense coverage of FIG. 5. In one embodiment, the cutting tips have an outside diameter "D" and an average inter-strand distance "I", as illustrated in FIG. 5, where I is about 2 to 3 times the value of D. The pattern of cutting tips can be controlled by utilizing radially outwardly biased cutting tips, which splay outward as illustrated in FIG. 4. The amount of splay is controlled in one embodiment by allowing the enclosing sheath to retract, allowing the cutting tips to splay further outward. Sheath 52 can prevent uncontrolled flopping of distal cutting tips 56, which can present a problem when large inter-strand distances are required, as with some mechanical cutting tips. The coverage of the cutting tips in FIG. 5 allows creation of a complete pattern of channels in the myocardium without requiring repositioning of the cutting tips.

In use, probe 50 can be positioned near the ventricle wall region to be revascularized, and RF current delivered through distal cutting tips 56. The resulting myocardial channels can be formed substantially at the same time, and a similar pattern delivered to an adjacent ventricular wall area soon thereafter.

In another embodiment of the invention, not requiring illustration, a radiopaque marker can be delivered and secured to a position in the ventricular wall. Suitable radiopaque materials include barium, bismuth, tungsten and platinum. Markers believed suitable include metal markers having barbs or pigtails to securely engage the ventricle wall. Other markers, such as radiopaque gels injected into the ventricular wall, are suitable provided they stay in place for the length of the procedure. Such markers are preferably injected from within the ventricle utilizing a catheter. A preferred method utilizes the cutting tip to first plant or inject a marker, followed by the cutting of a series of channels in the myocardium. By utilizing a radiopaque distal cutting tip and a fixed, implanted radiopaque marker, the relative positions of the two can be viewed fluoroscopically and adjusted fluoroscopically, thereby allowing formation of a controlled pattern of channels. The radiopaque marker provides a reference point for forming a pattern of channels in the myocardium.

In another embodiment of the invention, the cutting tip injects radiopaque material in conjunction with the cutting of a channel. In this embodiment, as each channel is formed, a radiopaque marker is left, creating a pattern of radiopaque markers viewable fluoroscopically. The pattern of channels formed in the myocardium are thus immediately viewable, giving feedback to the treating physician as to the progress and scope of the pattern of channels. Suitable materials for injection into the myocardium are preferably biodegradable or absorbable into the body soon after the procedure, allowing the myocardial channels to be perfused with blood. A device suitable for cutting and injection of material is described in copending U.S. patent application Ser. No. 08/812,425, filed Mar. 16, 1997, entitled TRANSMYOCARDIAL CATHETER AND METHOD, herein incorporated by reference.

Referring now to FIG. 6, left ventricle 34 having a magnetically anchorable, positionable PMR device 86 device within is illustrated. PMR device 86 is similar in some respects to PMR device 20 illustrated in FIG. 1, with device 86 differing primarily at the distal end of anchoring shaft 26. Anchoring shaft 26 has a magnetically responsive portion 80 at the anchoring shaft distal end. "Magnetically responsive" as used herein refers to a material capable of being attracted or repelled by a magnet. Magnetically responsive portion 80 can be used in conjunction with external magnets to position anchoring shaft 26 against the ventricle wall. External magnets such as magnet 84 can be disposed external to the body, positioned to direct the distal end of anchoring shaft 26 into the center of a target area in the heart. In one embodiment, the external magnets are rare earth magnets. In another embodiment, the external magnets are superconducting magnets. In a preferred embodiment, several magnets 84 are used to direct anchoring shaft 26 into the heart wall.

In use, magnets 84 can be used in conjunction with axially moving anchoring shaft 26 to plant anchoring shaft 26 in the desired location. Pairs of magnets in all three dimensions may not be required as the goal is to pull the anchoring shaft against a ventricle wall, not necessarily to suspend it in place using the magnets. The magnets, in conjunction with a radiopaque anchoring shaft tip and fluoroscopy, can be used to guide the anchoring shaft into position and maintain position during treatment. In the embodiment illustrated, an anchoring spike 82 lies at the distal end of anchoring shaft 26. Anchoring spike 82, drawn larger in FIG. 6 than in the preferred embodiment, is used to stabilize the position of the anchoring shaft distal end once the desired position has been reached. Another embodiment terminates anchoring shaft 26 without any spike, rather ending with magnet 80. Still another embodiment terminates anchoring shaft 26 with an orifice, such as a suction tip, in communication with a vacuum lumen within shaft 26, allowing anchoring shaft 26 to be held in place by applying vacuum to the vacuum lumen and orifice, thereby securing the distal tip of shaft 26 with vacuum pulling against the heart chamber wall.

Referring now to FIG. 7, a heart 35 having a PMR catheter 90 disposed within. PMR catheter 90 includes a shaft 92, illustrated extending through the aorta and into left ventricle 34. A magnetically response distal portion 94 is located near a distal cutting tip 96 on PMR catheter 90. As illustrated, cutting tip 96 has been guided into left ventricular wall 36 and has cut a channel in the wall. External magnets 84 can be used to position cutting tip 96 into the desired position with the aid of fluoroscopy. Distal portion 94 is preferably radiopaque, to aid in guiding cutting tip 96 into position. As PMR catheter shaft 92 provides some degree of support to cutting tip 96, and as the primary goal is to pull cutting tip 96 into the ventricular wall, pairs of magnets in all three dimensions may not be required. External magnets 84 serve to position cutting tip 96, and, with the assistance of catheter shaft 92, can serve to pull cutting tip 96 into the ventricular wall.

Referring now to FIG. 8, a magnetically responsive catheter 100 is illustrated, disposed within heart 35, being extended through aorta 102 into a left coronary artery 104. Catheter 100 includes a magnetically responsive distal region 106, which can be attracted by external magnets 84. Catheter 100 can be used in conjunction with external magnets to stabilize regions of the heart, lessening the amount of wall movement due to the beat of the heart.

In use, magnetically responsive catheter 100 can be advanced with aid of fluoroscopy through the aorta and into a coronary artery. Catheter distal region 106 preferably includes radiopaque materials to aid positioning under fluoroscopy. Once in position, distal region 106 is effectively located in the heart wall. When stabilization is desired, external magnets such as magnet 84 can be positioned near catheter distal region 106. By exerting a strong pull on distal region 106, the movement of the heart wall in the vicinity of catheter distal region 106 can be lessened.

Stabilization can be used during intravascular PMR procedures, minimally invasive PMR procedures, and heart procedures generally. When used during PMR procedures, the stabilization can serve to lessen heart wall movement in the area being cut. When used during other medical procedures, the stabilization can serve to minimize heart wall movement in areas being operated on or otherwise treated. When used during intravascular PMR procedures, a second, PMR catheter should be provided.

Figure 9:
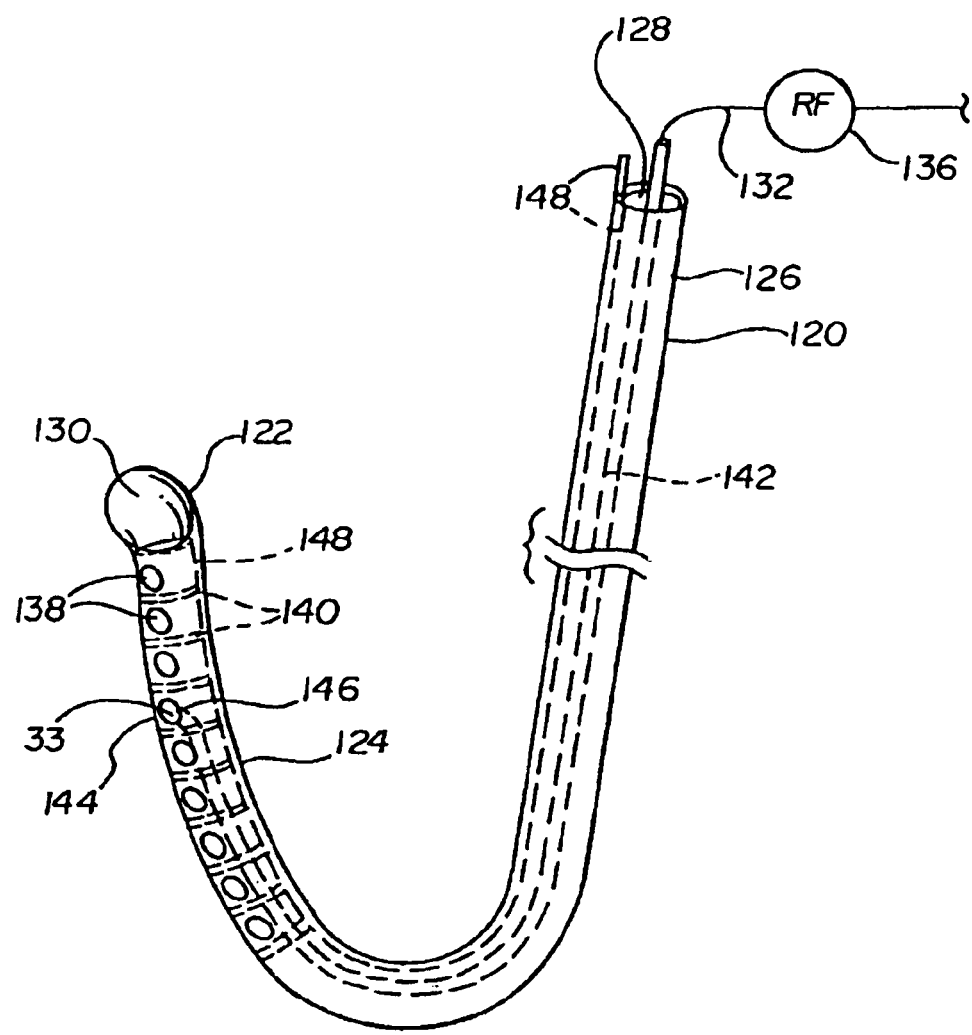
FIG. 9 is a perspective view of a multiple channel positioning device for forming multiple myocardial channels in a ventricle wall, having distal anchoring means and containing a guide catheter containing a PMR cutting wire, both drawn in phantom.

Referring now to FIG. 9, a multiple-channeled PMR positioning device or guiding tube 120 is illustrated. Positioning tube 120 includes a distal end 122, a distal region 124, a proximal end 126, a plurality of channels 138 within distal region 124, and a lumen 128 therethrough. A distal anchoring means 130 is preferably located distal of distal region 124 and can serve to fix the position of distal end 122 to the wall of the left ventricle or other heart chamber. In one embodiment, anchoring means 130 includes an orifice or suction tip in communication with a vacuum lumen 148, such that anchoring means 130 can be held in place against a heart chamber wall once positioned near the wall. In another embodiment, anchoring means 130 includes a magnetically responsive material such that an externally applied magnetic field can force anchoring means 130 into a heart chamber wall. In this magnetically responsive embodiment, anchoring means 130 can be similar to distal portion 94 illustrated in FIG. 7. In another embodiment, tube distal region 124 is magnetically responsive and can be similar to magnetically responsive region 106 illustrated in FIG. 8. Distal tip 122 is preferably formed of soft, atraumatic material and distal region 124 formed of sufficiently pliable material so as to allow distal region 124 to conform to a ventricle wall.

Disposed within positioning tube 120 is a guide catheter 142 extending from positioning tube proximal end 126 to distal region 124. Disposed within guide catheter 142 is a PMR cutting wire 132, proximally electrically connected to an RF energy source 136 and terminating distally in a cutting tip 33. PMR wire 132 includes a distal arcuate or bent region 144 proximate distal cutting tip 33. Arcuate region 144 can be bent or arced so as to have a performed shape or bias to extend laterally away from the longitudinal axis of the PMR wire. In one embodiment, PMR wire lies within positioning tube 120 directly, without a guide catheter. In a preferred embodiment, a guide catheter such as guide catheter 142 is disposed about the PMR wire. PMR wire 132 is slidably disposed within guide catheter 142 and can be rotated by applying torque to the proximal end.

In use, positioning tube 120 can be preloaded with guide catheter 142 containing PMR wire 132. PMR wire 132 can be retracted such that arcuate region 144 is retracted either to a position proximal of channels 138 or within positioning tube distal region 124 but retracted within guide catheter 142. In this retracted position, PMR wire arcuate region 144 does not extent from channels 138. With PMR wire retracted, positioning tube 120 can be advanced through the vasculature into a heart chamber such as the left ventricle. Positioning tube distal end 122 can be advanced down into the ventricle and up a ventricular wall. With distal end 122 in a desired position, anchoring means 130 can be used to anchor distal end 122 to the ventricular wall. In embodiments where anchoring means 130 is magnetically responsive or where positioning tube distal region 124 is magnetically responsive, an external magnetic force can be applied to pull or push anchoring means 130 and distal region 124 into the wall. In embodiments where anchoring means 130 is a suction tip, vacuum can be applied to the vacuum lumen in communication with the suction tip.

With positioning tube distal region 124 in place, guide catheter 142 containing PMR wire 132 can be advanced to push tube distal end 122 and PMR wire arcuate region 144 distally out of guide catheter 142. PMR wire 132 can be rotated such that cutting tip 33 is oriented toward channels 138, and guide catheter 142 and PMR wire 132 retracted together until cutting tip 33 can be pushed out of channel 138. Cutting tip 33 can be advanced through channel 138 and a channel cut into the myocardium. In a preferred embodiment, PMR wire 132 has a depth stop 146 proximal of arcuate region 144 that limits the length of wire passed through channels 138, such that the depth of a PMR formed myocardial channel is limited. After myocardial channel formation, PMR wire 132 can be retracted through the channel and the next, more proximal channel entered. In a preferred embodiment, arcuate region 144 is radiopaque and a series of radiopaque marker bands separate channels 138 to aid in positioning cutting tip 33. In one embodiment, PMR wire 132 can be rotated to cut more than one myocardial channel per positioning tube channel. In this manner, a series of myocardial channels in a regular pattern can be formed over the length of positioning tube distal region 124.

Referring now to FIG. 10, another embodiment positioning tube 160 is illustrated. Positioning tube 160 has a shape member 164 which can assist in forming the U-shape of tube 160 illustrated in FIG. 10. In one embodiment, shape member 164 is formed of a shape memory material such as Nitinol and embedded within the wall of tube 160 to impart a shape to the tube once tube 160 is within a ventricle and is no longer as restrained as when disposed within a blood vessel or guide catheter. In another embodiment, shape member 164 is a pull wire slidably disposed within a lumen within tube 160 and fixedly attached to a distal portion of the tube as indicated at 166. In this embodiment, shape member 164 can be pushed and pulled from a proximal location outside of the patient's body so as to assist in imparting a shape to tube distal region 124. In FIG. 10, the distal most portion of tube 160, including anchoring means 130, has been omitted from the drawing to more clearly illustrate the distal termination of shape member 164. From inspection of FIG. 10, it may be seen that, by rotating positioning tube 160 to different anchoring positions, and by advancing PMR wire 132 to various tube channels, a large expanse of ventricular wall can be covered and have myocardial channels formed therein.

Referring now to FIG. 11, a tube-in-a-tube embodiment positioning device 180 is illustrated. Positioning device 180 includes an inner PMR cutting probe 182 slidably disposed within an intermediate tube 184 which is slidably disposed within an outer tube 186. PMR probe 182 has a cutting tip 188 and preferably has radiopaque marker bands 190. Marker bands 190 aid in positioning the PMR probe under fluoroscopy. PMR probe 182 is preferably performed to have an arcuate or bent distal region 192.

Intermediate tube 184 has a channel 194 formed through the tube wall sufficiently large to allow passage of PMR probe 182. In a preferred embodiment, channel 194 is formed in a side tube wall in a distal portion of intermediate tube 184, as illustrated in FIG. 11. Outer tube 186 has an anchoring tip 200 and a slot 196, with slot 196 illustrated extending along the longitudinal axis of the outer tube. Slot 196 is sufficiently wide to allow passage of PMR probe 182 therethrough. In one embodiment, anchoring tip 200 is formed of a soft material and held in place by axial force directed along the longitudinal axis of device 180. In another embodiment, anchoring tip 200 contains a magnetically responsive material and is held in place at least partially by externally applied magnetic forces. Referring now to FIG. 12, a section of PMR probe 182 is further illustrated, showing one structure for imparting a performed arc or bend to the probe. PMR probe 182 can include a tube wall 199 having a perform wire 198 embedded therein. Perform wire 198 is preferably formed of a shape memory material such as Nitinol, such that the arcuate or bent shape is reformed upon exit from the constraint of intermediate tube 184.

Referring again to FIG. 11, the wide range of motion possible for cutting tip 188 may be discussed. The radial extent of cutting tip 188, the distance from the center longitudinal axis of outer tube 186, can be varied by extending PMR probe 182, thereby forcing a longer extent of exposed probe through intermediate tube channel 194 and through outer tube slot 196. As PMR probe 182 has arcuate region 192 in a preferred embodiment, extending PMR probe also changes the longitudinal position of the cutting tip as more arc is exposed. Sliding intermediate tube 184 within outer tube 186 also changes the longitudinal position of cutting tip 188. Cutting tip 188 is illustrated at a first position A in FIG. 11, a second, more distal position B, and a third, still more distal position C, as intermediate tube 184 is advanced distally within outer tube 186. Finally, outer tube 186 can be rotated about its center, longitudinal axis, thereby extending the range of coverage of cutting tip 188.

In use, PMR positioning device 180 can be advanced into the left ventricle and anchoring tip 200 forced against some portion of the vermicular wall. Intermediate tube 184 can be slid within outer tube 186 to a desired position. Inner PMR probe 182 can be advanced out of channel 194 until the desired length of PMR probe is exposed. A desired position of cutting tip 188 can be reached by adjusting the length of PMR probe 182 exposed, the length of intermediate tube 184 advanced into outer tube 186, and the rotation of outer tube 186. In one method, a series of arcs of myocardial channels are formed substantially transverse to the longitudinal axis of positioning device 180. In this method, outer tube 186 is rotated such that cutting tip 188 describes an arc. As each arc is completed, intermediate tube 184 is slid relative to outer tube 186 and a new arc of channels is burned into the ventricular wall.

Referring now to FIG. 13, an extendable collar embodiment PMR positioning device 220 is illustrated. Device 220 includes inner PMR probe 182 disposed within an intermediate tube or sleeve 222 which is slidably disposed within an outer collar 224. Intermediate sleeve 222 includes a distal end 240 and has a lumen 242 extending therethrough. Inner PMR probe 182 is preferably slidable within intermediate sleeve 222. Device 220 includes an elongate rod 226 having a distal region 228 secured to outer collar 224. In a one embodiment, elongate rod 226 is capable of both pulling and pushing outer collar 224 over intermediate sleeve 222. An elongate anchoring member 230 includes a proximal region 236, a distal end 234, a distal anchoring means such as pigtail 234, and can be slidably and rotatably secured to outer collar 224.

In one embodiment, elongate rod 226 and anchoring member 230 are both slidably disposed in a dual lumen tube 227 substantially coextensive with intermediate tube 222. Dual lumen tube 227 can terminate the lumen containing elongate rod 226 in a skived portion 229, continuing the tube as a single lumen portion 231. Single lumen portion 231 allows elongate rod 226 to freely travel with outer collar 224. Outer collar 224 preferably is slidably disposed over single lumen portion 231.

Intermediate sleeve 238 and inner PMR probe 182 together have an arcuate or bent bias or perform, as illustrated at 238. In one embodiment, intermediate sleeve 222 has a performed shape which can be imparted with an embedded shape wire as illustrated by wire 189 in FIG. 12. In another embodiment, PMR probe 182 has an arcuate bias sufficiently strong to impart a distal bend to both intermediate sleeve 238 and PMR probe 182 when outer collar 224 is retracted. PMR probe 182 can include Nitinol or other shape memory material to impart this arcuate bias. In yet another embodiment, both inner PMR probe and intermediate sleeve 238 have a performed arcuate or bent distal shape.

In one embodiment, intermediate tube 222 can be rotated within outer collar 224. In another embodiment, intermediate tube is restricted in rotation corresponding ridges and grooves between outer collar 224 and intermediate tube 222. In one embodiment, outer collar has internal ridges fitting within external grooves in a region of intermediate tube 222. Restricting the rotation of intermediate tube 222 within collar 224 can aid in causing rotation about anchoring member 230 rather than about the center of outer collar 224.

In use, outer collar 224 can be extended distally over intermediate sleeve 222, such that collar 224 is proximate intermediate sleeve distal end 240. Inner PMR probe 182 can be preloaded within intermediate sleeve 222. With outer collar 224 distally extended, arcuate region 238 is substantially restrained and straightened. Device 220 can be advanced within the vasculature and into a heart chamber such as the left ventricle. Elongate anchoring member 230 can be advanced distally and rotated, thereby rotating pigtail 232 into the ventricle wall and securing anchoring member 230. With intermediate sleeve 222 and PMR cutting tip 188 positioned as indicated at "E" in FIG. 13, the extent of PMR probe exposed can be adjusted by axially sliding PMR probe 182 within intermediate sleeve 222. The extent of intermediate sleeve extending distally beyond collar 224 can be adjusted in some embodiments by advancing or retracting sleeve 222 within collar 224. With PMR cutting tip 188 in position, intermediate sleeve 222 can be rotated about anchor member 230 and a circular pattern of myocardial channels can be burned about the pigtail. In a variant method, possible in devices allowing rotation of intermediate sleeve 222 within outer collar 224, intermediate sleeve 222 can be rotated about the center axis of outer collar 224. With one circle completed, outer collar 224 can be retracted, allowing more of the performed shape of sleeve 22 and PMR probe 182 to appear, as illustrated, for example, at "D" in FIG. 13. As collar 224 is retracted, PMR probe 182 can be advanced to describe circular paths of increasing radius over the inner ventricle walls. In this way, a series of circular paths of myocardial channels about the anchoring point can be formed in the ventricle walls. In one embodiment, elongate member 226 is capable of only retracting collar 224, which, once retracted within the ventricle, cannot be advanced within the ventricle. In another embodiment, elongate member 226 is capable of both advancing and retracting collar 224 over intermediate sleeve 222. With the formation of myocardial channels complete, anchoring member 226 can be rotated opposite the initial rotation, thereby releasing pigtail 232 from the ventricle wall.

Figure 14:
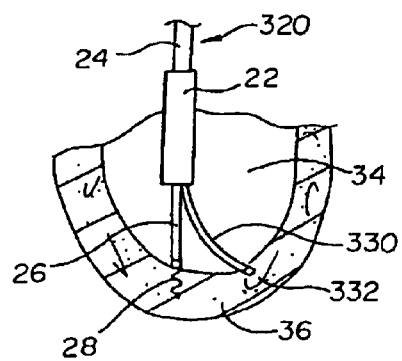
FIG. 14 is a fragmentary, side, cutaway view of a left ventricle having an anchorable, positionable cryanoblative PMR device within.

FIG. 14 illustrates an anchorable, cryanoblative PMR treatment catheter 320 disposed within a left ventricle 34. The term "cryanoblative", as used herein, refers to the delivery of cold sufficient to cause tissue death. Similarly numbered elements are discussed with respect to FIG. 1. Cryanoblative catheter 320 includes an inner star shaft 24 disposed within an outer catheter shaft 22, an anchoring shaft 26 disposed within star shaft 24, and a cryanoblative treatment tube 330 disposed within catheter shaft 22. Cryanoblative treatment tube 330 is preferably formed of metal and can include a distal cryanoblative tip 332 and a lumen through which a cold substance, such as liquid nitrogen, is delivered.

In one embodiment, distal cryanoblative tip 332 includes a distal orifice in communication with the treatment shaft lumen, such that liquid nitrogen can be delivered through the orifice and to the heart chamber wall. In another embodiment, tube 330 is close ended and initially under vacuum, allowing liquid nitrogen to be delivered to the tube distal region, causing the tube to become very cold without allowing liquid nitrogen to enter the myocardium. The cryanoblative tip can be inserted into the heart chamber wall, penetrating the wall, and into the myocardium prior to delivery of liquid nitrogen. The delivery of liquid nitrogen to the heart chamber wall can cause localized tissue death, bringing about the same healing response as laser and radio-frequency current PMR.

Figure 15:
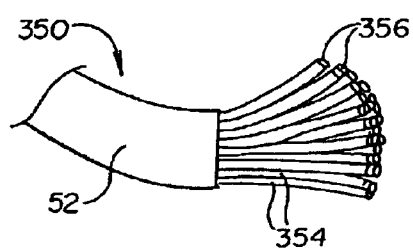
FIG. 15 is a fragmentary, perspective view of a multiple-tip cryanoblative PMR treatment device according to the present invention.

Referring now to FIG. 15, a multi-tube, cryanoblative treatment probe 350 is illustrated. Treatment probe 350 includes a plurality of cryanoblative tubes 354, having distal cryanoblative cutting tips 356, and enclosed within a sheath 52. In one embodiment, tubes 354 are feed from a common supply within sheath 52, such that tubes 354 have a short length, with most of the length lying distal of the sheath. Probe 350 allows a pattern of channels to be formed in the myocardium at the same time, not requiring repeated repositioning of a single cutting tip such as cutting tip 332 of FIG. 14. The pattern of cutting tips can be controlled by utilizing radially outwardly biased cutting tips, which splay outward as illustrated in FIG. 15. The amount of splay is controlled in one embodiment by allowing the enclosing sheath to retract, allowing the cutting tips to splay further outward. Sheath 52 can prevent uncontrolled flopping of distal cutting tips 356, which can present a problem when large inter-strand distances are required, as with some mechanical cutting tips.

The coverage of the cutting tips in FIG. 15 allows creation of a complete pattern of channels in the myocardium without requiring repositioning of the cutting tips. The resulting myocardial channels can be formed substantially at the same time, and a similar pattern delivered to an adjacent ventricular wall area soon thereafter. As discussed with respect to FIG. 14, cryanoblative tubes 354 can be formed of metal and be either closed or open ended.

In a variation of the methods previously described, a radiopaque contrast media is used to determine the depth of channels formed in the myocardium. The contrast medium is injected or "puffed" into or near the channel formed in the myocardium. The heart can be visualized under fluoroscopy to determine the depth of the channel formed thus far. After visualization, the channel can be further deepened. The cycle of channel formation, contrast medium puffing, and fluoroscopic visualization can be repeated until the channel has the desired depth.

Contrast medium could be injected using a lumen such as the lumen of guide catheter 142 of FIG. 9. A lumen such as the lumen in tube 330 of FIG. 14 could also be used to deliver contrast medium. The lumens previously discussed with respect to injecting liquid nitrogen could be used to deliver contrast medium.

In addition to using the device as described herein above to form channels in the myocardium, the device could be used to form craters in the myocardium. That is, to form a wound in the myocardium having a width greater than its depth. The crater can be formed by controlling the depth of insertion of, for example, a radiofrequency device and/or controlling the power delivered to the distal tip of the device such that a crater is formed. Those skilled in the art can also appreciate that mechanical devices, laser devices or the like could be used to form craters.

In use, the above methods and devices can be used to form a pattern of channels leading from healthy myocardial tissue to hibernating tissue. This can operate by multiple mechanisms to supply hibernating tissue with an increased blood supply. First, channels in the myocardium can perfuse tissue directly from the ventricle, through the patent channel formed by the cutting tip. Second, the channels formed by the cutting tip can become newly vascularized by operation of a healing response to the channel injury. The new blood vessels thereby increase further the supply of hibernating tissue by ventricular blood. Third, the series of newly formed vessels caused by the healing response can form interconnections or anastomoses between the series of injured areas, forming a network of blood vessels, which, by connecting with healthy area vessels, can be supplied by blood originating from coronary arteries in addition to blood supplied directly by the ventricle.

Figure 16:
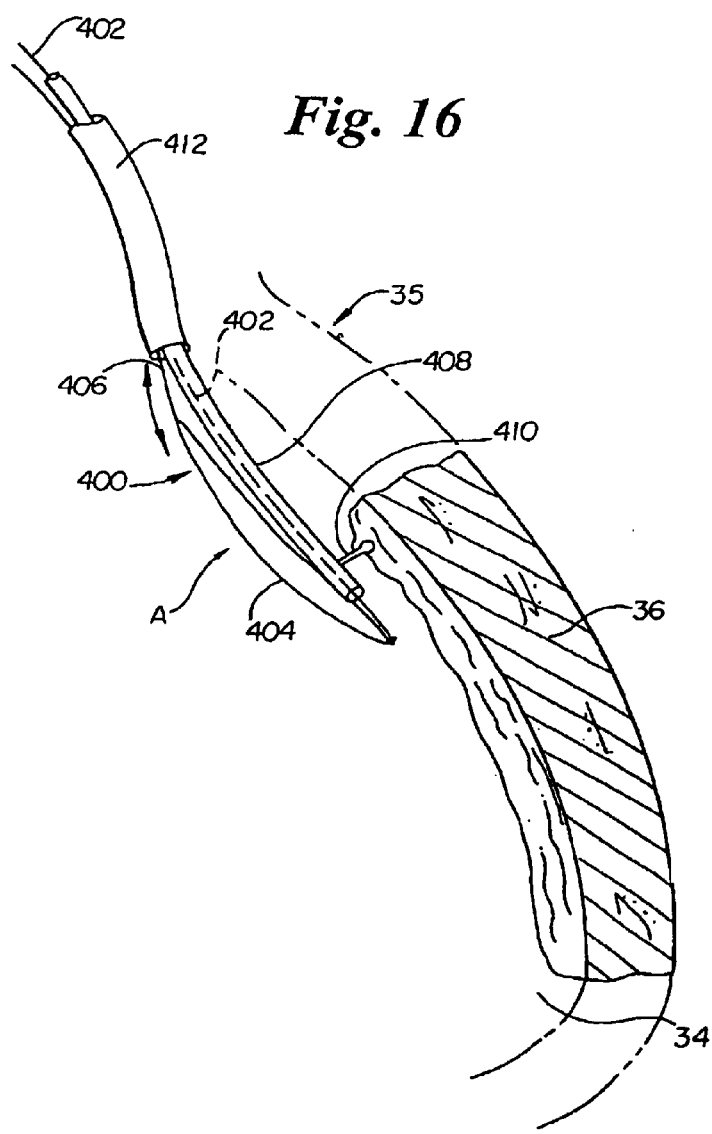
FIG. 16 is a perspective view of yet another embodiment of the device in accordance with the present invention.

FIG. 16 shows yet another embodiment of the present invention in the form of catheter assembly 400. Here only the distal end of catheter assembly 400 is shown disposed within the left ventricle of a patient's heart. Those skilled in the art will appreciate the various configurations possible for the proximal end of the catheter in view of the description of the distal end which follows. Catheter assembly 400 includes an elongate guide wire 402 having a distal end and a proximal end. A collapsible loop 404 is hingably connected to the distal end of guide wire 402. A retraction member 406 is hingably connected to loop 404 opposite the connection to guide wire 402. Therapeutic catheter 408, which has a lumen extending therethrough, is shown advanced over guide wire 402. Catheter 408 has a distal end and a proximal end, and proximate the distal end of catheter 408 is a therapeutic member 410. Therapeutic member 410 can be an elongate electrode having a ball tip. In a preferred embodiment, a conductor extends through catheter 408 to deliver RF energy to electrode 410. Electrode 410 can be hingably connected to catheter 408 such that catheter assembly 400 can be advanced through a guide catheter 412.

The materials to be used, and the methods of fabrication, to make catheter assembly 400 will be known to one skilled in the art in view of the uses to which catheter assembly 400 are put. As shown in FIG. 16, loop 404 is disposed in a first collapsed position A. In collapsed position A, loop 404 is advancable to left ventricle 34 of heart 35 by a percutaneous route through the aorta. FIG. 17 shows loop 404 in a second position B deployed within left ventricle 34. When loop 404 is in second position B, a portion of guide wire 402 lies near and approximately parallel to left ventricle wall 36, while a portion of loop 404 abuts the opposite wall. In this position, catheter 408 can be advanced as shown by the arrow along guide wire 402. As catheter 408 is advanced, electrode 410 can be energized repeatedly to form holes or channels 442 in wall 36. A further series of holes 442 can be formed by rotating wire 402 and loop 404 as shown by the arrows adjacent loop 404.

In order to move loop 404 between first position A and second position B, guide wire 402 should be relatively rigid in comparison to loop 404 and actuator member 406. With that configuration, actuator 406 can be pulled proximately to move loop 404 from second position B to first position A. In turn, actuator member 406 can be moved distally to deploy loop 404.

FIG. 18 is a view of the distal end of catheter 408 showing an alternate therapeutic device. In particular, a hypodermic needle 414 is shown extending from distal end 408. Hypodermic needle 414 is preferably hingable connected to catheter 408 such that it can be advanced and withdrawn through a guide catheter. If catheter 408 includes an infusion lumen, contrast media, growth factor or other drug can be delivered to wall 36 through needle 414.

FIG. 19 is a view of the distal end of catheter 408 showing yet another therapeutic device disposed thereon. In particular, an electrode 416 is shown which has a length greater than the distance which it extends transversely from catheter 408. Such an electrode can be used to form a crater 444 having a width greater than its depth.

FIG. 20 is a view of the distal end of catheter 408 showing another therapeutic device disclosed thereon. In FIG. 20 an abrasive burr 418 is shown extending transversely from catheter 408. When rotated, burr 14 can form a crater 444. In both FIGS. 19 and 20, electrode 416 and burr 418 are shown spaced from heart wall 36. While creating craters 444, it is understood that loop 404 will be deployed in second position B such that electrode 416 and burr 418 will be in contact with heart wall 36.

It can be appreciated that each of the devices disclosed herein can be bi-polar as well as mono-polar. To make a bi-polar configuration, a ground electrode would need to be disposed on the device proximate the electrode(s) shown.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A device for guiding a percutaneous myocardial revascularization cutting wire distal region to a plurality of heart chamber wall sites comprising:
   an elongate outer tube having a tubular wall and a distal region, said distal region wall having a plurality of channels therethrough;
   an elongate shape member on said outer tube and secured to said outer tube wall over at least said outer tube distal region,
      said shape member having a performed shape such that said outer tube distal region is biased to assume said shape member performed shape, and;
   means for stabilizing the position of said outer tube distal region within said heart chamber from within the heart, wherein the stabilizing means is magnetically responsive to an externally-generated magnetic field,
   such that said percutaneous myocardial revascularization cutting wire distal region can be advanced through said outer tube distal region wall channels to said heart chamber wall sites.

2. A device for guiding a PMR cutting wire as recited in claim 1, wherein said means for stabilizing said outer tube position includes a magnetically responsive portion of said outer tube distal region, such that an externally applied magnetic field can exert a force upon said outer tube distal region.

3. A device for creating a plurality of myocardial channels in a heart chamber wall comprising:
   an elongate outer tube having a tubular wall and a distal region, said distal region wall having a plurality of channels therethrough;
   an elongate shape member on said outer tube and secured to said outer tube wall over at least said outer tube distal region,
      said shape member having a performed shape such that said outer tube distal region is biased to assume said shape member performed shape,
   means for stabilizing the position of said outer tube distal region within said heart chamber from within the heart, wherein the stabilizing means is magnetically responsive to an externally-generated magnetic field; and
   a percutaneous myocardial revascularization cutting wire having a distal region disposed within said outer tube, such that said percutaneous myocardial revascularization cutting wire distal region can be advanced through said outer tube distal region wall channels to said heart chamber wall.

4. A device as recited in claim 3, further comprising a guide tube disposed about said PMR cutting wire and disposed within said tube.

5. A device as recited in claim 3, wherein said PMR cutting wire distal region has a distal tip such that said distal region is predisposed to extend through said outer tube channels when said distal tip is passed over said channels.

6. A device as recited in claim 3, wherein said means for stabilizing said outer tube position includes a magnetically responsive portion of said outer tube distal region, such that an externally applied magnetic field can exert a force upon said outer tube distal region.

7. A device for creating a plurality of myocardial channels in a heart chamber wall comprising:
   an elongate outer tube having a longitudinal axis, a proximal end, a distal end, a tubular wall, a distal region, said distal region wall having an elongate slot therethrough, said slot having a length, and an anchoring tip located substantially at a distal end of said distal region;
   an elongate intermediate tube disposed within said outer tube, said intermediate tube having a wall, a distal region, and a channel in said distal region wall; and
   an elongate inner percutaneous myocardial revascularization cutting probe disposed within said intermediate tube and adapted to extend through said intermediate tube channel such that a distal length of said percutaneous myocardial revascularization cutting probe extends outside of said intermediate and outer tubes, wherein said percutaneous myocardial revascularization cutting probe extends at a longitudinal position relative to said outer tube,
   said outer tube slot having a proximal portion and a distal portion, said intermediate tube being slidable within said outer tube, said inner percutaneous myocardial revascularization cutting probe being slidable within said intermediate tube, such that said percutaneous myocardial revascularization probe extended distal length can be varied by sliding said inner percutaneous myocardial revascularization probe within said intermediate tube and through said intermediate tube channel, such that said percutaneous myocardial revascularization probe longitudinal position can be varied by sliding said intermediate tube within said slot, such that said percutaneous myocardial revascularization probe can be rotated by rotating said outer tube.

8. A device as recited in claim 7, wherein said anchor tip is made of a resilient material and is adapted to rest against said heart chamber wall and stabilize said outer tube when an axial force is applied to said outer tube.

9. A device as recited in claim 7, wherein said anchor tip includes a magnetically responsive portion, such that an externally applied magnetic field can exert a force upon said outer tube distal region.

* * * * *